United States Patent [19]

Katre et al.

[11] Patent Number: 4,766,106

[45] Date of Patent: Aug. 23, 1988

[54] SOLUBILIZATION OF PROTEINS FOR PHARMACEUTICAL COMPOSITIONS USING POLYMER CONJUGATION

[75] Inventors: Nandini Katre, El Cerrito; Michael J. Knauf, Oakland, both of Calif.

[73] Assignee: Cetus Corporation, Emeryville, Calif.

[21] Appl. No.: 148,145

[22] Filed: Jan. 25, 1988

Related U.S. Application Data

[63] Continuation of Ser. No. 866,459, May 21, 1986, abandoned, which is a continuation-in-part of Ser. No. 749,955, Jun. 26, 1985, abandoned.

[51] Int. Cl.$^4$ ...................... A61K 37/02; C07K 13/00
[52] U.S. Cl. ......................................... 514/12; 514/2; 530/351; 424/85; 424/83
[58] Field of Search ...................... 424/85, 83; 514/12, 514/2; 530/351

[56] References Cited

U.S. PATENT DOCUMENTS

| | | |
|---|---|---|
| 3,619,371 | 11/1971 | Crook et al. . |
| 3,788,948 | 1/1974 | Kagedal et al. . |
| 3,876,501 | 4/1975 | Hanushewsky . |
| 3,960,830 | 6/1976 | Bayer et al. . |
| 4,002,531 | 1/1977 | Royer . |
| 4,055,635 | 10/1977 | Green et al. . |
| 4,088,538 | 5/1978 | Schneider . |
| 4,179,337 | 12/1979 | Davis et al. . |
| 4,261,973 | 4/1981 | Lee et al. . |
| 4,301,144 | 11/1981 | Iwashita et al. . |
| 4,412,989 | 11/1983 | Iwashita et al. . |
| 4,414,147 | 11/1983 | Klibanov et al. . |
| 4,415,665 | 11/1983 | Mosbach et al. . |
| 4,495,285 | 6/1985 | Shimizu et al. . |
| 4,496,689 | 6/1985 | Mitra . |
| 4,609,546 | 9/1986 | Hiratani . |

FOREIGN PATENT DOCUMENTS

| | | |
|---|---|---|
| 0098110 | 1/1984 | European Pat. Off. . |
| 0147761 | 7/1985 | European Pat. Off. . |
| 0152847 | 8/1985 | European Pat. Off. . |
| 154316 | 9/1985 | European Pat. Off. . |
| 154596 | 9/1983 | Japan . |
| 86/04145 | 7/1986 | PCT Int'l Appl. . |

OTHER PUBLICATIONS

Boccu et al., Z. Naturforsch, Sec. C., vol. 38c, No. 1/2, issued Jan./Feb. 1983, pp. 94–99.
Gary E. Means, "Methods in Enzymology, 47, 469–478 (1977).
Inada et al., Biochem., and Biophys. Res. Comm., vol. 122, pp. 845–850 (1984).
Takahashi et al., Biochem. and Biophys. Res. Comm., vol. 121, pp. 261–265, 1984.
Suzuki et al., Biochem. Biophys. Acta, vol. 788, pp. 248–255 (1984).
Abuchowski et al., Cancer Biochem. Biophys., vol. 7, pp. 175–186 (1984).
Davis et al., Biomedical Polymers, New York: Academic Press, 1980, pp. 441–451.

*Primary Examiner*—Blondel Hazel
*Attorney, Agent, or Firm*—Albert P. Halluin; Janet E. Hasak

[57] ABSTRACT

A pharmaceutical composition is prepared wherein a biologically active conjugated protein which is β-interferon, interleukin-2, or an immunotoxin is dissolved in an aqueous carrier medium without the presence of a solubilizing agent. The unconjugated protein, which is not water-soluble or not readily soluble in water at pH 6–8 without such solubilizing agent, is selectively conjugated to a water-soluble polymer selected from polyethylene glycol homopolymers or polyoxyethylated polyols.

15 Claims, 6 Drawing Sheets

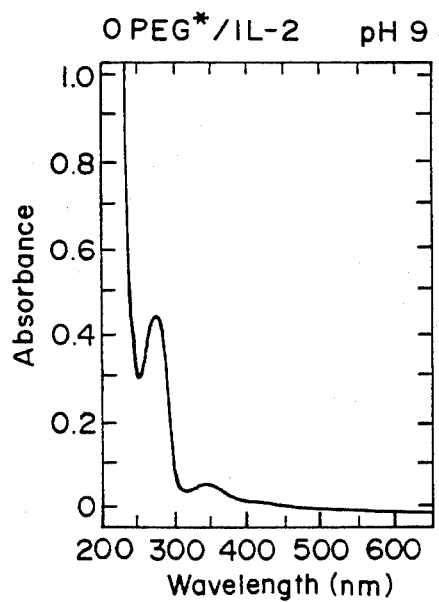
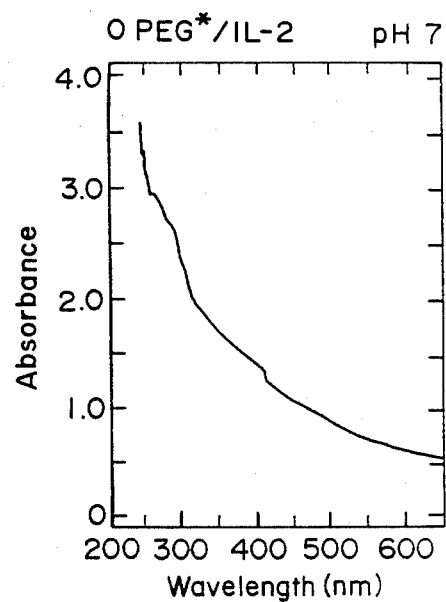
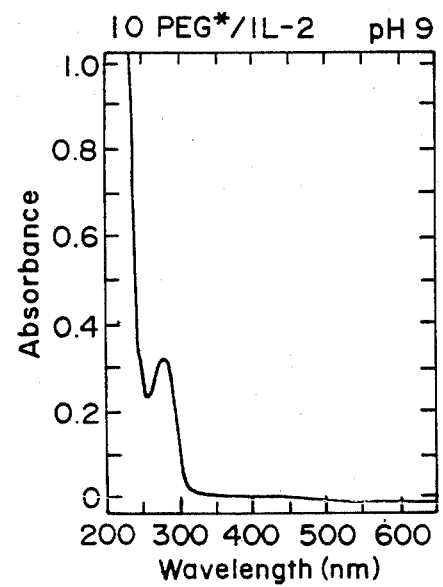
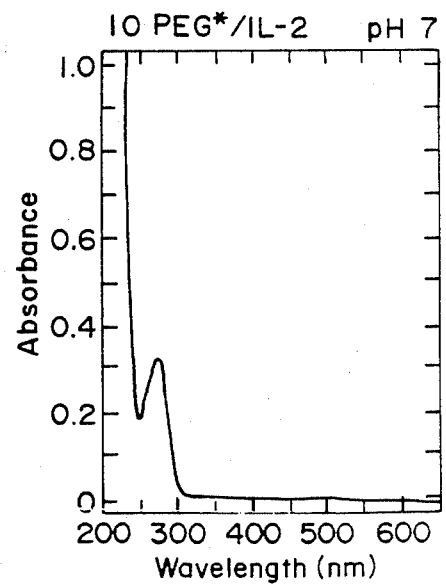
FIG. 2

SOLUBILIZATION OF PROTEINS FOR PHARMACEUTICAL COMPOSITIONS USING POLYMER CONJUGATION

This application is a continuation of application Ser. No. 866,459, filed May 21, 1986, now abandoned, which is a continuation-in-part of U.S. application Ser. No. 749,955, filed June 26, 1985, now abandoned.

BACKGROUND OF THE INVENTION

This invention relates to a chemical modification of biologically active proteins which alters the chemical and/or physiological properties of these proteins. More specifically, this invention relates to selective conjugation of lipophilic water-insoluble proteins to polymers to render the proteins soluble at physiological pH.

Many heterologous proteins produced in microbial host cells are found as insoluble material in refractile bodies. Examples of heterologous proteins which form refractile bodies in commonly found culture conditions include interleukin-2 (IL-2), interferon-$\beta$ (IFN-$\beta$), feline leukemia virus (FeLV) envelope protein, human growth hormone (hGH), bovine growth hormone (bGH), porcine growth hormone (pGH), and certain proteins coated or fused with a virus such as FMD virus. In addition, many of these proteins are hydrophobic in nature and tend to stick to materials and to themselves (i.e., aggregate) rather than remain in solution. Also, many of these recombinant proteins are unglycosylated, whereas their native counterparts are water-soluble, glycosylated molecules. Modifications of these proteins which might alter their solubility properties would be desirable to increase production yields of these proteins as well as to facilitate their formulation for therapeutic use. In addition, modifications may reduce or eliminate aggregation of the protein when it is introduced in vivo, thereby reducing its immunogenicity.

The use of polypeptides in circulatory systems for the purpose of producing a particular physiological response is well known in the medicinal arts. A limitation to the potential therapeutic benefit derived from the clinical use of polypeptides is their ability to elicit an immune response in the circulatory system. This immune response may be caused by aggregates in the material prior to injection as described by R. Illig (1970), *J. Clin. Endrocr.*, 31, 679–688, W. Moore (1978), *J. Clin. Endrocrinol. Metab.*, 46, 20–27 and W. Moore and P. Leppert (1980), *J. Clin. Endrocrinol. Metab.*, 51, 691–697. This response involves the production of antibodies to the polpeptides by the circulatory system into which they are injected. This antibody production may descrease or eliminate the desired biological function of the polypeptide, sometimes by causing reduced residence time in the circulatory system (reduced half-life) or by modifying the molecule by virtue of the antibody-polypeptide interaction.

Modification of these potentially useful therapeutic polypeptides so as to preclude or at least reduce an immune respose while still maintaining desired physiological activities of the polypeptide would allow the use of these polypeptides in the mammalian circulatory system without the aforementioned disadvantages. In addition, due to the increased half-life of the circulating polypeptide, smaller amounts of the polypeptide would be required for the desired therapeutic effect than have heretofore been possible.

The problems of immunogenicity and short half-life in circulation set forth hereinabove and other undesirable properties of certain proteins are well recognized and various modifications of polypeptides have been undertaken to solve them. These include the modification of proteins with substantially straight chain polymers such as polyethylene glycol (PEG) or polypropylene glycol (PPG). For example, U.S. Pat. No. 4,261,973 describes conjugation of immunogenic allergen molecules with non-immunogenic water-soluble polymers such as PEG to reduce the immunogenicity of the allergen. U.S. Pat. No. 4,301,144 describes conjugation of hemoglobin to PEG, PPG, a copolymer of ethylene glycol with propylene glycol, or ethers, esters or dehydrated products of such polymers to increase the oxygen-carrying ability of the hemoglobin molecule. European Patent Publication No. 98,110, published Jan. 11, 1984, discloses that conjugating of a polypeptide or glycoprotein to a polyoxyethylene-polyoxypropylene copolymer increases the length of its physiological activity. Preferably the polypeptide or glycoprotein is an enzyme or native interferon, which are water soluble. U.S. Pat. No. 4,179,337 discloses conjugating of water-soluble polypeptides such as enzymes and insulin to PEG or PPG to reduce the immunogenicity of the polypeptide while retaining a substantial proportion of its desired physiological activity. U.S. Pat. No. 4,002,531 discloses a different method of conjugating enzymes to PEG through an aldehyde derivative.

U.S. Pat. No. 4,055,635 discloses pharmaceutical compositions comprising a water-soluble complex of a proteolytic enzyme linked covalently to a polymeric substance such as polysaccharides.

U.S. Pat. No. 3,960,830 discloses peptides bound to a polyalkylene glycol polymer such as polyethylene glycol.

U.S. Pat. No. 4,088,538 discloses a reversibly soluble enzymatically active polymer enzyme product comprising an engyme covalently bonded to an organic polymer such as polyethylene glycol.

U.S. Pat. No. 4,415,665 discloses a method of conjugating an organic ligand containing at least one primary or secondary amino group, at least one thiol group and/or at least one aromatic hydroxy group (described in col. 3, lines 19–36) to a polymeric carrier with at least one hydroxyl group (described in col. 2, lines 42–66).

U.S. Pat. No. 4,495,285 discloses a non-immunogenic plasminogen activator, the amino acid side chains of which are coupled to a polyalkylene glycol through a coupling agent.

U.S. Pat. No. 4,412,989 discloses an oxygen-carrying material containing hemoglobin or a derivative thereof covalently coupled through an amide bond to polyethylene or polypropylene glycol.

U.S. Pat. No. 4,496,689 discloses a covalently attached complex of alpha-1-proteinase inhibitor with a polymer such as PEG or methoxypolyethylene glycols.

U.S. Pat. No. 3,619,371 discloses a polymeric matrix having a biologically active substance chemically bound thereto.

U.S. Pat. No. 3,788,948 discloses use of organic cyanate compounds to bind proteins to polymers.

U.S. Pat. No. 3,876,501 discloses activation of water-soluble carbohydrates with cyanogen bromide to improve their binding to enzymes and other proteins.

U.S. Pat. No. 4,055,635 discloses pharmaceutical compositions of a proteolytic enzyme linked covalently to a polymeric substance.

EP No. 152,847 discloses an enzyme conjugate composition comprising an enzyme conjugate, a calcium salt, and a polyethylene glycol.

JP No. 5792435 published Nov. 26, 1982 discloses modified polypeptides were all or part of the amino groups are substituted with a polyethoxyl moiety. DE No. 2312615 published Sept. 27, 1973 discloses conjugating of polymers to compounds containing hydroxy or amino groups.

EP No. 147,761 discloses a covalent conjugate of alpha-1-proteinase inhibitor and water-soluble polymer, where the polymer may be polyethylene glycol.

U.S. Pat. No. 4,414,147 describes rendering interferon less hydrophobic by conjugating it to an anhydride of a dicarboxylic acid such as poly(ethylene succinic anhydride).

In addition to these patents and patent publications, several articles discuss the concept of using activated PEG or PPG as a modifying agent for proteins such as enzymes, IgG and albumin. For example, Inada et al., *Biochem and Biophys. Res. Comm.*, 122, 845–850 (1984) disclose modifying water-soluble lipoprotein lipase to make it soluble in organic solvents such as benzene by using cyanuric chloride to conjugate with PEG. Takahashi et al., *Biochem. and Biophys. Res. Comm.*, 121, 261–265 (1984) disclose modifying horseradish peroxidase using cyanuric chloride triazine with PEG to make the water-soluble enzyme active and soluble in benzene. Suzuki et al., *Biochem. Biophys. Acta*, 788, 248–255 (1984) disclose suppression of aggregation of IgG using cyanuric chloride activated PEG. Abuchowski et al., *Cancer Biochem. Biophys.*, 7, 175–186 (1984) state that modification of asparaginases from *E. coli* and *Vibrio succinogenes* using PEG activated by succinimidyl succinate increases the half-life and decreases the immunogenicity of the proteins. Davis et al., *Biomedical Polymers*, (New York: Academic Press, 1980), p. 441–451 disclose that enzymes normally insoluble may be solubilized by PEG attachment without further details. Several other articles discuss modification of enzymes such as uricase, streptokinase, catalase, arginase and asparaginase with PEG activated by succinimidyl succinate or cyanuric chloride to increase half-life and decrease the immunogenicity of the protein.

None of these references, however, disclose details on how to use a polymer modification process to water-solubilize recombinant proteins such as IL-2 and IFN-β which are hydrophobic and therefore resist formulation in an aqueous medium at physiological pH. Furthermore, it is not a priori possible to predict which selected proteins would be favorably responsive to treatment with polymers due to the vast difference in the pharmacokinetics and physical properties of various proteins. Furthermore, none of the references disclose reducing or eliminating aggregation of the protein, a phenomenon that elicits an immune response when the protein is introduced in vivo.

EP No. 154,316, published Sept. 11, 1985 to Takeda Chemical Industries, Ltd., discloses and claims chemically modified lymphokines such as IL-2 containing PEG bonded directly to at least one primary amino group of a lymphokine.

SUMMARY OF THE INVENTION

Accordingly, the present invention provides for modifying those proteins selected from β-interferon, interleukin-2, and immunotoxins which are not ordinarily soluble in water under ambient conditions at pharmaceutically acceptable pH ranges to render them soluble in aqueous buffer under such conditions. This modification may be mimicking glycosylation of the protein, thereby surprisingly rendering the protein soluble as the native glycosylated protein is soluble. This modification also avoids addition of extraneous solubilizing additives such as detergents or denaturants to keep the protein in solution. The modified protein retains the biological activity of the unmodified protein, both initially and over time.

As secondary advantages, the modification under some conditions increases the physiological half-life of the protein and may decrease its immunogenicity by reducing or eliminating aggregation of the protein or by masking antigenic determinants. It has also been found that this prolonged half-life is related to the efficacy of the protein. The in vivo half-life can be modulated by selecting appropriate conditions and polymers.

More specifically, the present invention is directed to a pharmaceutical composition comprising a non-toxic, inert, pharmaceutically acceptable aqueous carrier medium in which is dissolved a biologically active selectively conjugated protein selected from the group consisting of β-interferon, interleukin-2, and an immunotoxin, wherein the protein is covalently conjugated to a water-soluble polymer selected from the group consisting of polyethylene glycol homopolymers and polyoxyethylated polyols, wherein said homopolymer is unsubstituted or substituted at one end with an alkyl group, and said polyol is unsubstituted, and wherein said protein in its unconjugated form is normally hydrophobic and not soluble in said aqueous carrier medium at pH 6–8 in the absence of a solubilizing agent.

Preferably the polymer is unsubstituted polyethylene glycol (PEG), monomethyl PEG (mPEG), or polyoxyethylated glycerol (POG), and it is coupled to the protein via an amide linkage formed from the 4-hydroxy-3-nitrobenzene sulfonate ester or the N-hydroxysuccinimide ester of a PEG, mPEG, or POG carboxylic acid.

Another aspect of this invention resides in a process for preparing a pharmaceutical composition comprising:

(a) preparing a water-soluble polymer having at least one terminal reactive group where the polymer is selected from the group consisting of polyethylene glycol homopolymers and polyoxyethylated polyols, wherein said homopolymer is unsubstituted or substituted at one end with an alkyl group and said polyol is unsubstituted;

(b) reacting a biologically active normally hydrophobic, water-insoluble protein selected from the group consisting of β-interferon, interleukin-2, and an immunotoxin with the reactive group of said polymer so as to provide a water-soluble, biologically active, selectively conjugated protein; and (c) formulating said protein in a non-toxic, inert, pharmaceutically acceptable aqueous carrier medium.

BRIEF DESCRIPTION OF THE DRAWINGS

FIG. 2 illustrates the solubility of PEGylated IL-2 compared to unmodified IL-2 at two different pHs by absorbance scan from 200 to 650 nm.

DESCRIPTION OF THE PREFERRED EMBODIMENT

Figure 1:
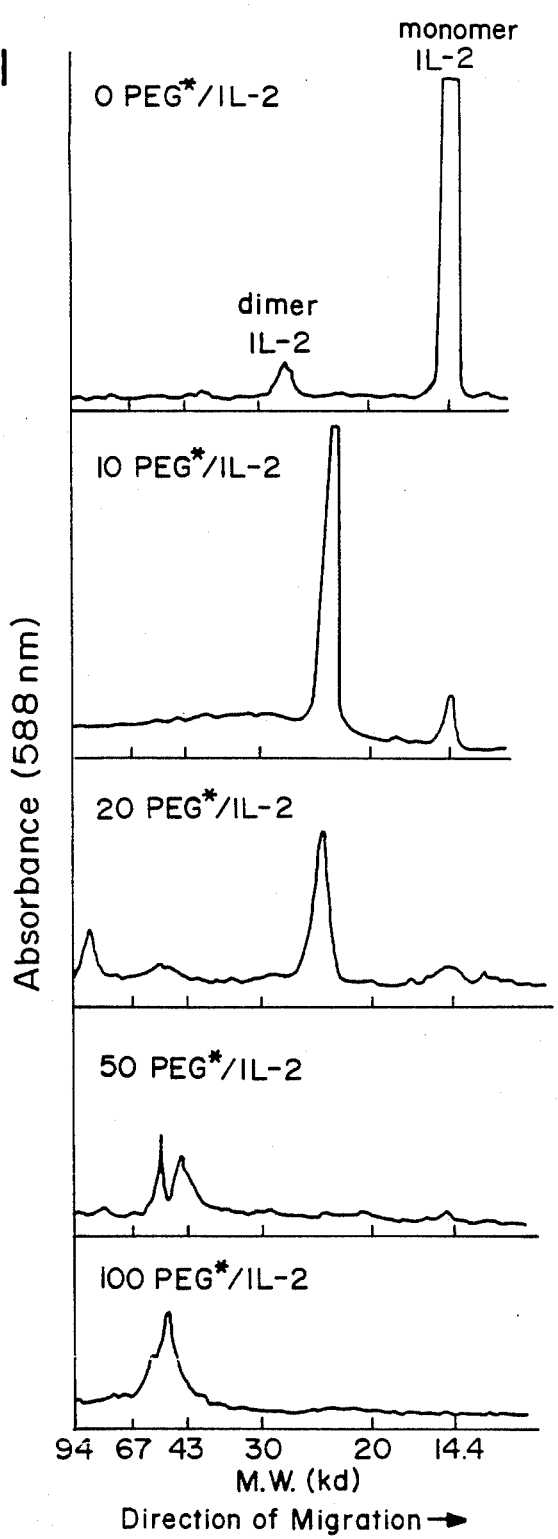
FIG. 1 shows densitometry scans of 14% SDS-polyacrylamide gels for molecular weight analysis of PEG-modified (PEGylated) IL-2 obtained from reactions at 0, 10, 20, 50 and 100 moles activated PEG (PEG*) per mole of IL-2.

As used herein, the term "normally hydrophobic, water insoluble" describing the proteins refers to those proteins which are insoluble or not readily soluble in water or an aqueous medium under ambient conditions of room temperature and atmospheric pressure at a pH of between about 6 and 8, i.e., at about neutral or physiological pH. The modification herein acts to increase the solubility of such proteins when they are subjected to such physiological conditions. For purposes herein, solubility may be tested by (1) turbidity, as measured by spectrophotometric means, (2) S value, as measured by ultracentrifugation, wherein the monomeric protein sedimentation rate rather than the much greater aggregate sedimentation rate signals solubility, and (3) apparent native molecular weight, as measured by size exclusion chromatography, wherein the soluble protein is closer to this value than the insoluble protein. The exact numbers which would indicate solubility for each of these tests will depend on the type of buffer in which the protein is formulated, the pH of the buffer, and the ionic strength of the buffer.

The interferon-$\beta$ and interleukin-2 herein may be obtained from tissue cultures or by recombinant techniques, and from any mammalian source such as, e.g., mouse, rat, rabbit, primate, pig, and human. Preferably such proteins are derived from a human source, and more preferably are recombinant, human proteins.

The term "recombinant $\beta$-interferon," designated as IFN-$\beta$, preferably human IFN-$\beta$, refers to fibroblast interferon having comparable biological activity to native IFN-$\beta$ prepared by recombinant DNA techniques as described in the art. In general, the gene coding for interferon is excised from its native plasmid and inserted into a cloning vector to be cloned and then into an expression vector, which is used to transform a host organism, preferably a microorganism, and most preferably $E.$ $coli.$ The host organism expresses the foreign interferon gene under certain conditions to produce IFN-$\beta$. More preferably, the IFN-$\beta$ is a mutein as described in U.S. Pat. No. 4,588,585, in which the cysteine normally occurring at position 17 of the wild-type or native molecule has been replaced by a neutral amino acid such as serine or alanine. Most preferably, the IFN-$\beta$ mutein is IFN-$\beta_{ser17}$.

The term "recombinant interleukin-2," designated as IL-2, preferably human IL-2, refers to interleukin-2 having comparable biological activity to native IL-2 prepared by recombinant DNA techniques as described, e.g., by Taniguchi et al., $Nature,$ 302: 305–310 (1983) and Devos, $Nucleic$ $Acids$ $Research,$ 11: 4307–4323 (1983). In general, the gene coding for IL-2 is excised from its native plasmid and inserted into a cloning vector to be cloned and then into an expression vector, which is used to transform a host organism, preferably a microorganism, and most preferably $E.$ $coli.$ The host organism expresses the foreign gene to produce IL-2 under expression conditions.

More preferably the IL-2 is a mutein as described in U.S. Pat. No. 4,518,584, in which the cysteine normally occurring at position 125 of the wild-type or native molecule has been replaced by a neutral amino acid such as serine or alanine. Alternatively or conjunctively, the IL-2 mutein may be one as described in copending U.S. application Ser. No. 810,656 filed Dec. 17, 1985, the disclosure of which is incorporated herein by reference, in which the methionine normally occurring at position 104 of the wild-type or native molecule has been replaced by a neutral amino acid such as alanine.

Preferably, the IL-2 is a protein produced by a microorganism or by yeast which has transformed with the human cDNA sequence of IL-2 which encodes a protein with an amino acid sequence at least substantially identical to the amino acid sequence of native human IL-2, including the disulfide bond of the cysteines at positions 58 and 105, and has biological activity which is common to native human IL-2. Substantial identity of amino acid sequences means the sequences are identical or differ by one or more amino acid alterations (deletions, additions, substitutions) which do not cause an adverse functional dissimilarity between the synthetic protein and native human IL-2. Examples of IL-2 proteins with such properties include those described by Taniguchi et al., supra; Devos, supra; European Patent Publication Nos. 91,539 and 88,195; U.S. Pat. No. 4,518,584, supra, and copending U.S. application Ser. No. 810,656 filed Dec. 17, 1985, supra. Most preferably, the IL-2 is ser$_{125}$IL-2, des-ala$_1$ser$_{125}$IL-2, des-ala$_1$IL-2, des-ala$_1$ala$_{104}$IL-2, or des-ala-$_1$-ala$_{104}$ser$_{125}$IL-2, where "des-ala$_1$" indicates that the N-terminal alanyl residue of the IL-2 has been deleted.

The precise chemical structure of the proteins herein will depend on a number of factors. As ionizable amino and carboxyl groups are present in the molecule, a particular protein may be obtained as an acidic or basic salt, or in neutral form. All such preparations which retain their bioactivity when placed in suitable environmental conditions are included in the definition of proteins herein. Further, the primary amino acid sequence of the protein may be augmented by derivatization using sugar moieties (glycosylation) or by other supplementary molecules such as lipids, phosphate, acetyl groups and the like, more commonly by conjugation with saccharides. Certain aspects of such augmentation are accomplished through post-translational processing systems of the producing host; other such modifications may be introduced in vitro. In any event, such modifications are included in the definition of protein herein so long as the bioactivity of the protein is not destroyed. It is expected, of course, that such modifications may quantitatively or qualitatively affect the bioactivity by either enhancing or diminishing the activity of the protein in the various assays.

Often the hydrophobic recombinant proteins such as IL-2 and IFN-$\beta$ produced from transformed host cells containing recombinant DNA precipitate inside the cell as opposed to being soluble in the cell culture medium. The intracellularly produced protein must be separated from the cellular debris and recovered from the cell before it can be formulated into a purified biologically active material. Commonly owned copending U.S. application Ser. No. 749,951 filed on June 26, 1985, entitled "Process for Recovering Refractile Bodies Containing Heterologous Proteins From Microbial Hosts" to W. Hanisch et al., the entire disclosure of which is incorporated herein by reference, discloses a process for isolating such a refractile material. In this process the cell membrane of the transformed host microorganism is disrupted, greater than 99% by weight of the salts is removed from the disruptate, the desalted disruptate is redisrupted, a material, preferably a sugar such as sucrose, is added to the disruptate to create a density or viscosity gradient in the liquid within the disruptate, and the refractile material is separated from the cellular debris by high-speed centrifugation, i.e., at about 10,000 to 40,000×g. Preferably, the salts are removed from the disruptate by diafiltration or centrifugation and sucrose is added to increase the density of the liquid to about 1.1 to 1.3 g/ml.

After the centrifugation step, the pellet containing the refractile bodies is solubilized with a denaturant such as sodium dodecyl sulfate, the resulting suspension is centrifuged, and the supernate containing the protein is treated to isolate the protein. The protein is separated from the supernate by appropriate means such as reverse-phase high pressure liquid chromatography (RP-HPLC) and/or gel filtration chromatography. After such separation, the protein is preferably oxidized to ensure the production of high yields of recombinant protein in a configuration most like its native counterpart. Such oxidation is described in U.S. Pat. No. 4,530,787 to Z. Shaked et al., the disclosure of which is incorporated herein by reference. The oxidation may also be carried out by reacting an aqueous solution containing a solubilized form of the protein at a pH between about 5.5 and 9 in the presence of air with at least an effective amount of an oxidation promoter containing a $Cu^{+2}$ cation, as described in U.S. Pat. No. 4,572,798 to K. Koths et al., the disclosure of which is incorporated herein by reference. The preferred oxidation promoter or oxidant is $CuCl_2$ or (o-phenanthroline)$_2Cu^{+2}$. After oxidation, the protein may optionally be desalted and purified further by RP-HPLC, dilution/diafiltration, S-200 gel filtration chromatography, and ultrafiltration techniques before modification with activated polymer as described further hereinbelow. The polymer modification may, however, be carried out at any step after the heterologous protein has been isolated in sufficiently pure form to be biologically active for therapeutic purposes. The point at which the modification will occur will depend on the ultimate purity of the protein required for the final pharmaceutical formulation and use.

The term "immunotoxin" as used herein to apply to the third class of proteins refers to a conjugate of an antibody and a cytotoxic moiety. The cytotoxic moiety of the immunotoxin includes a cytotoxic drug or an enzymatically active toxin of bacterial or plant origin or an enzymatically active fragment ("A chain") of such a toxin. Examples of enzymatically active toxins and fragments thereof include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), momordica charantia inhibitor, curcin, crotin, saponaria officinalis inhibitor, gelonin, mitogellin, restrictocin, phenomycin, and enomycin. Ricin A chain, nonbinding active fragments of diphtheria toxin, abrin A chain, and PAPII are preferred. Most preferred is the ricin A chain, which is modified by reaction with the polymer.

The antibodies employed in the immunotoxin are preferably monoclonal antibodies directed against a specific pathological condition such as, e.g., cancers such as breast, prostate, colon or ovarian cancer, melanoma, myeloma, etc.

Conjugates of the antibody and cytotoxic moiety may be made using a variety of bifunctional protein modifying reagents. Examples of such reagents include N-succinimidyl-3-(2-pyridyldithio) propionate (SPDP), iminothiolate (IT), bifunctional derivatives of imidoesters such as dimethyl adipimidate.HCl, active esters such as disuccinimidyl suberate, aldehydes such as glutaraldehyde, bis-azido compounds such as bis (p-azidobenzoyl) hexanediamine, bis-diazonium derivatives such as bis-(p-diazonium-benzoyl)-ethylenediamine, diisocyanates such as tolylene-2,6-diisocyanate, and bis-active fluorine compounds such as 1,5-difluoro-2,4-dinitrobenzene.

The term "selectively conjugated" as used herein to apply to the protein refers to proteins which are covalently bonded via one or more of the amino acid residues of the proteins, depending mainly on the reaction conditions, the ultimate use, the molecular weight of the polymer, and the particular protein employed. While the residues may be any reactive amino acids on the protein, such as one or two cysteines or the N-terminal amino acid group, preferably the reactive amino acid is lysine, which is linked to the reactive group of the activated polymer through its free ε-amino group, or glutamic or aspartic acid, which is linked to the polymer through an amide bond.

In one preferred embodiment the protein is covalently bonded via one or two of the amino acid residues of the protein, preferably lysines, for maximum biological activity. In another preferred embodiment, the protein is covalently bonded via up to ten of the amino acid residues of the protein, preferably lysines, with higher substitutions generally increasing the circulatory life of the protein.

According to the process of this invention, the three types of proteins described above, which are normally hydrophobic and water insoluble, are rendered soluble in an aqueous carrier medium, preferably at a pH of about 5 to 8, more preferably about 6–8 and most preferably, 6.5–7.8, without use of a solubilizing agents, by modifying the proteins through conjugation to a specified polymer. If the protein is reacted through its lysine residues, the pH of the reaction is preferably about 7 to 9, more preferably 8–9. The success of such a modification of these proteins cannot be predicted from earlier use of polymer modification of water-soluble enzymes and hormones.

The polymer to which the protein is attached is a homopolymer of polyethylene glycol (PEG) or is a polyoxyethylated polyol, provided in all cases that the polymer is soluble in water at room temperature. Examples of polyoxyethylated polyols include, for example, polyoxyethylated glycerol, polyoxyethylated sorbitol, polyoxyethylated glucose, or the like.

The glycerol backbone of polyoxyethylated glycerol is the same backbone occurring naturally in, for example, animals and humans in mono-, di-, and triglycerides. Therefore, this branching would not necessarily be seen as a foreign agent in the body.

The polymer need not have any particular molecular weight, but it is preferred that the molecular weight be between about 300 and 100,000, more preferably between 350 and 40,000, depending, for example, on the particular protein employed.

Preferably the PEG homopolymer is unsubstituted, but it may also be substituted at one end with an alkyl group. Preferably the alkyl group is a $C_1-C_4$ alkyl group, and most preferably a methyl group. Most preferably, the polymer is an unsubstituted homopolymer of PEG, a monomethyl-substituted homopolymer of PEG or polyoxyethylated glycerol, and has a molecular weight of about 350 to 40,000.

The protein is conjugated via a terminal reactive group on the polymer. The polymer with the reactive group(s) is designated herein as activated polymer. The reactive group selectively reacts with free amino or other reactive groups on the protein. It will be understood, however, that the type and amount of the reactive group chosen, as well as the type of polymer employed, to obtain optimum results, will depend on the protein employed to avoid having the reactive group react with too many particularly active groups on the protein. As this may not be possible to avoid completely, it is recommended that generally from about 0.1 to 1000 moles, preferably 2-200 moles, of activated polymer per mole of protein, depending on protein concentration, is employed. For IL-2 in particular, the amount of activated polymer employed is preferably no more than 50 moles per mole of IL-2, and most preferably is about 2 to 20 moles per mole of IL-2, depending on the specific properties ultimately desired, i.e., the final amount is a balance to maintain optimum activity, while at the same time optimizing, if possible, the half-life of the protein. Preferably, at least about 50% of the biological activity of the protein is retained, and most preferably 100% is retained.

The covalent modification reaction may take place by any suitable method generally used for reactive biologically active materials with inert polymers, preferably at about pH 5-9, if the reactive groups on the protein are lysine groups. Generally the process involves preparing an activated polymer (with at least one terminal hydroxyl group) and thereafter reacting the protein with the activated polymer to produce the solubilized protein suitable for formulation.

The above modification reaction can be performed by several methods, which may involve one or more steps. Examples of suitable modifying agents which can be used to produce the activated polymer in a one-step reaction include cyanuric acid chloride (2,4,6-trichloro-S-triazine) and cyanuric acid fluoride.

In a preferred embodiment the modification reaction takes place in two steps wherein the polymer is reacted first with an acid anhydride such as succinic or glutaric anhydride to form a carboxylic acid, and the carboxylic acid is then reacted with a compound capable of reacting with the carboxylic acid to form an activated polymer with a reactive ester group which is capable of reacting with the protein. Examples of such compounds include N-hydroxysuccinimide, 4-hydroxy-3-nitrobenzene sulfonic acid, and the like, and preferably N-hydroxysuccinimide or 4-hydroxy-3-nitrobenzene sulfonic acid is used. For example, monomethyl substituted PEG may be reacted at elevated temperatures, preferably about 100°–110° C. for four hours, with glutaric anhydride. The monomethyl PEG-glutaric acid thus produced is then reacted with N-hydroxysuccinimide in the presence of a carbodiimide reagent such as dicyclohexyl or isopropyl carbodiimide to produce the activated polymer, methoxypolyethylene glycolyl-N-succinimidyl glutarate, which can then be reacted with the protein. This method is described in detail in Abuchowski et al., *Cancer Biochem. Biophys.*, 7, 175–186 (1984). In another example the monomethyl substituted PEG may be reacted with glutaric anhydride followed by reaction with 4-hydroxy-3-nitrobenzene sulfonic acid (HNSA) in the presence of dicyclohexyl carbodiimide to produce the activated polymer. HNSA is described in Bhatnagar et al., *Peptides: Synthesis-Structure-Function, Proceedings of the Seventh American Peptide Symposium*, Rich, et al. (eds.) (Pierce Chemical Co., Rockford IL, 1981), p. 97–100, and in Nitecki et al., *High-Technology Route to Virus Vaccines* (American Society for Microbiology: 1986) entitled "Novel Agent for Coupling Synthetic Peptides to Carriers and Its Applications."

As ester bonds are chemically and physiologically less stable than amide bonds, it may be preferable to use chemical transformations in the conjugating reaction which would produce carboxylic acids or amides without concurrent production of esters.

The protein thus modified is then formulated in a non-toxic, inert, pharmaceutically acceptable aqueous carrier medium, preferably at a pH of about 3 to 8, more preferably 6–8. For in vitro applications, as for immunotoxins used for diagnostic purposes, the modes of administration and formulation are not critical. Aqueous formulations compatible with the culture or perfusion medium will generally be used. When used in vivo for therapy, the sterile product will consist of a mixture of protein dissolved in an aqueous buffer in an amount which will provide a pharmaceutically acceptable pH when the mixture is reconstituted. A water-soluble carrier such as mannitol may optionally be added to the medium. The currently formulated unmodified IL-2 is stable for at least six months at 4° C.

The dosage level of protein in the formulation will depend on the in vivo efficacy data obtained after preclinical testing and will depend mainly on the protein employed and ultimate use.

If the formulation is lyophilized, the lyophilized mixture may be reconstituted by injecting into the vial a conventional parenteral aqueous injection such as, e.g., distilled water.

The reconstituted formulation prepared as described above is suitable for parenteral administration to humans or other mammals in therapeutically effective amounts (i.e., amounts which eliminate or reduce the patient's pathological condition) to provide therapy thereto, the type of therapy being dependent on the type of protein. For example, IL-2 therapy is appropriate for a variety of immunomodulatory indications such as T cell mutagenesis, induction of cytotoxic T cells, augmentation of natural killer cell activity, induction of IFN-gamma, restoration or enhancement of cellular immunity (e.g., treatment of immune deficient conditions), and augmentation of cell mediated anti-tumor activity.

In an alternative to direct administration of IL-2, the IL-2 may be administered in an adoptive immunotherapy method, together with isolated, lymphokine-activated lymphocytes, in a pharmaceutically acceptable carrier, where the lymphocytes are reactive to tumor when administered with the IL-2 to humans suffering from the tumor. This method is described more fully in copending U.S. application Ser. No.

763,657 entitled "IL-2/Adoptive Immunotherapy" filed Aug. 8, 1985 (NTIS), and by S. Rosenberg et al., *New England Journal of Medicine* (1985), 313:1485–1492.

IFN-β therapy is appropriate for anti-cancer, antiviral and anti-psoriasis treatment. Specific cancers against which IFN-β has shown some efficacy include lymphoma, myeloma, hairy-cell leukemia and some viral diseases including venereal warts and rhinoviruses.

Immunotoxin therapy is appropriate for diseases against which the targeted antibody is effective, usually cancer. In particular, immunotoxins are being targeted for such cancers as breast cancer.

The dose and dosage regimen of the immunotoxin will depend, for example, upon the pharmacokinetics of the drug, the nature of the cancer (primary or metastatic) and its population, the type and length of polymer, the characteristics of the particular immunotoxin, e.g., its therapeutic index, the patient, and the patient's history. The dose and dosage regimen of the IL-2 and IFN-β will similarly depend, for example, on the pharmacokinetics of the drug, the nature of the disease, the characteristics of the IL-2 or IFN-β, the patient and the patient's history. For example, different modified IL-2 proteins are expected to have different pharmacokinetic and therapeutic properties which are advantageous for different routes of administration. A long-acting drug might only be administered every 3–4 days, every week or once every two weeks. The clearance rate can be varied to give ultimate flexibility to fit the particular need of the patient by changing, e.g., the type of polymer and the size of the polymer attached.

In the following examples, which illustrate the invention further, all parts and percentages are by weight unless otherwise noted, and all temperatures are in degrees Celsius.

EXAMPLE I

Preparation of PEGylated Interleukin-2 (IL-2)

A. Preparation of PEG-Ester

A linear, monomethyl substituted ester of PEG of molecular weight 5000 can be obtained by first reacting monomethyl PEG-5000, which is commercially available, with glutaric anhydride at 100° to 110° C. for four hours or by a method similar to that of Abuchowski et al., *Cancer Biochem. Biophys.*, 7, 175–186 (1984), the disclosure of which is incorporated herein by reference. The resulting PEG-glutarate is reacted with N-hydroxysuccinimide in the presence of dicyclohexylcarbodiimide, as described in detail by Abuchowski et al., supra, on page 176. The resulting product is methoxypolyethylene glycolyl N-succinimidyl glutarate, hereinafter designated as PEG*.

Similarly, succinic anhydride was reacted with monomethyl PEG-5000 and the resulting PEG-succinate was reacted with N-hydroxysuccinimide. The resulting product is methoxypolyethylene glycolyl N-succinimidyl succinate.

In an alternative step, and by a similar method, a PEG carboxylic ester-HNSA was prepared using HNSA in place of N-hydroxysuccinimide. This ester preparation is described by Bhatnagar et al., supra and by Nitecki et al., supra. The PEG carboxylic ester-HNSA may be used as the activated PEG in the procedures described in this and subsequent examples.

B. Conjugating of PEG* to IL-2

RP-HPLC purified recombinant des-alanyl, ser$_{125}$ IL-2 (where the cysteine at position 125 is replaced by serine and the N-terminal alanyl residue is deleted), prepared as described in U.S. Pat. Nos. 4,518,584 and 4,530,787, supra, or the post-diafiltered des-ala$_1$, ser$_{125}$ IL-2 from the production process described hereinabove, was employed for this example. To 0.5 mg of this purified IL-2 in 1.0 ml buffer (sodium borate, pH 9; 0.1% SDS) was added freshly prepared aqueous PEG* in molar ratios of 0, 2.5, 5, 10, 20, 50 and 100 moles PEG* per mole of IL-2. After thorough mixing, the solutions were stirred at room temperature (23° C.) for 30 minutes. Each reaction mixture was applied to a Sephadex G-25 column (Pharmacia) to separate IL-2 and PEG-IL-2 from low molecular weight species. The Sephadex G-25 column was run in 10 mM Na borate pH 9 containing no SDS and served also to remove most of the SDS from the protein. Most of the unmodified IL-2 and SDS was alternatively removed by adding the reaction mixture to a mixed bed ion retardation resin (Bio-Rad AG11A8). The level of residual SDS in the PEGylated IL-2 samples, as measured by the acridine-orange test, as described by R. Sokoloff and R. Frigon, *Anal. Biochem.*, 118, 138–141 (1981), was 3–7 μg SDS per mg protein.

C. Purification of Modified IL-2

Using hydrophobic exchange chromatography (Bio-Rad; Biogelphenyl-5-PW), purified PEGylated IL-2 was obtained. A linear gradient with decreasing salt (Solvent A is 1.7 M(NH$_4$)$_2$SO$_4$ in 50 mM Na phosphate pH 7; 100–0% A in 15 min.) gave good separation of PEGylated IL-2 and unmodified IL-2. Adding 10% ethanol to Solvent B and maintaining the column in an ice bath greatly enhanced the recovery and resolution, respectively, of PEGylated IL-2. Aliquots of the fractions were assayed for IL-2 bioactivity (cell proliferation) by the methods generally described in Gillis, S., et al., *J. Immunol.*, 120, 2027–2032 (1978).

EXAMPLE II

Characterization of PEGylated IL-2

A. Size characterization of modified IL-2 products from reactions with varying PEG to IL-2 molar ratios SDS-PAGE (14%) of the products from reactions described in Example I.A. containing 0, 10, 20, 50 or 100 moles PEG* per mole of IL-2 indicated an increasing degree of modification with increasing PEG* to IL-2 molar ratios. Densitometer scans of various gel lanes were obtained using a Shimadzu Dual Wavelength Scanner (CS-930) as shown in FIG. 1. The 10 PEG*/IL-2 and 20 PEG*/IL-2 samples showed a discrete species with an apparent molecular mass of approximately 25 kd in addition to small amounts of unmodified IL-2. At 50 PEG*/IL-2 and 100 PEG*/IL-2 there was a smear in the high molecular weight region, which is characteristic of extensively PEGylated proteins, and there was no unmodified IL-2.

Size exclusion of the PEG-IL-2 solutions on a TSK-250 column (Bio-Rad; 25×0.4 cm in PBS) provided further evidence of increasing modification with increasing PEG* to IL-2 ratios.

B. Bioactivity of PEGylated IL-2 as a Function of the Extent of Modification

Fractions from the aforementioned Biogel-phenyl column elutions of IL-2 PEGylation reactions containing 0, 2.5, 5, 10, 20, 50 or 100 moles PEG* per mole of IL-2 were assayed by the IL-2 cell proliferation bioassay described in Example I.C. The results are shown in Table I. As more amino groups were modified, the IL-2 was increasingly inactivated. In reactions carried out at a molar ratio of 100 PEG*/IL-2, the specific activity of the modified IL-2 product was significantly lowered to only about 10% of that of unmodified IL-2.

TABLE I

Bioactivity of PEGylated IL-2 as a Function of the Extent of Modification

| Mole of PEG-ester initially added per mole IL-2 | Bioactivity (BRMP Standards Units/mg IL-2)* |
|---|---|
| 1. 0 PEG*/IL-2 | $7.36 \pm 4.83 \times 10^6$ |
| 2. 2.5 PEG*/IL-2 | $9.20 \pm 3.45 \times 10^6$ |
| 3. 5 PEG*/IL-2 | $11.50 \pm 2.30 \times 10^6$ |
| 4. 10 PEG*/IL-2 | $10.35 \pm 4.37 \times 10^6$ |
| 5. 20 PEG*/IL-2 | $7.82 \pm 2.76 \times 10^6$ |
| 6. 50 PEG*/IL-2 | $3.45 \pm 2.30 \times 10^6$ |
| 7. 100 PEG*/IL-2 | $0.69 \pm 0.23 \times 10^6$ |

*These numbers reflect a large variability in the IL-2 bioassay.

C. Solubility of PEGylated IL-2 compared to Unmodified IL-2.

After the modification reaction and subsequent Sephadex G-25 chromatography resulting in SDS removal, the pH of the PEGylated IL-2 was lowered to 6.5-7. The unmodified IL-2 in the low SDS precipitated at pH 5-7. The modified IL-2 from the reaction carried out at low molar ratios in relation to the amounts of PEG*/IL-2 in Table I had some turbidity, due to unmodified IL-2 which can be subsequently removed by AG11A8 resin or Biogel phenyl (HPLC) chromatography. The solution of modified IL-2 from higher molar ratios of PEG*/IL-2 remained clear over time. The pH-adjusted solutions were ultracentrifuged (50,000 rpm, SW60 rotor, 12 hours at 5° C.). The supernatants were removed and stored. Analysis of aliquots of both the residues and the supernatants by SDS-PAGE showed that the residues were unmodified IL-2 while the supernatants contained PEGylated IL-2. The dramatic difference in the solubility of PEGylated and unmodified IL-2 in the aqueous medium at neutral pH, in the absence of SDS or any other denaturants, is illustrated by the absorbance scans (Hewlett-Packard 8450A Spectrophotometer) in FIG. 2. The unmodified IL-2 at pH 7 precipitates out of solution as evidenced by a loss of the characteristic spectrum.

Purified PEGylated IL-2 (after HPLC-phenyl column) was completely soluble at pH 7 in aqueous buffer without any detergent or denaturants. The purified PEGylated IL-2 remained in solution and retained its bioactivity over the time tested (at least five months). The PEGylated IL-2 which was soluble at neutral pH without SDS had the following specific activities compared to unmodified IL-2 in the presence of 0.1% SDS:

| Moles PEG* Initially Added Per Mole IL-2 | Specific Activity (BRMP Standards Units/mg IL-2) |
|---|---|
| 0 | $7.36 \times 10^6$ |
| 10 | $12.88 \times 10^6$ |
| 20 | $8.51 \times 10^6$ |

NK (Natural Killer; described in U.S. Pat. No. 4,518,584) and LAK (Lymphokine-Activated Killer; described in Grimm et al., J. Exp. Med., 155:1823-41 (1982)) activities of 10 PEG*/IL-2 and 20 PEG*/IL-2 were identical to those of unmodified IL-2. Addition of free PEG (4K daltons) in a 20-fold molar excess over unmodified IL-2 did not affect NK or LAK activities.

D. Stability of PEGylated IL-2 as a function of pH.

PEGylated IL-2 from a modification reaction using 50 moles PEG* per mole of IL-2 was incubated at various pH's at room temperature for three hours and then analyzed by 14% SDS-PAGE for hydrolysis of the amide-linked PEG from the IL-2 polypeptide. PEGylated IL-2 was three-fold diluted in 10% acetonitrile containing 0.1% trifluoroacetic acid (pH 2.5), and also incubated at pH 7.5, 10 and 11. Alkaline pH's were attained by the addition of NaOH to sodium borate buffer at pH 9. No evidence of hydrolysis was obtained below pH 11 under these conditions. However, at pH 11, the PEGylated IL-2 was susceptible to hydrolysis. The observation that PEGylated IL-2 is stable at pH 2.5 for three hours at room temperature (20°-23° C.) is particularly useful in view of U.S. Pat. No. 4,569,790 issued Feb. 11, 1986 describing a process for recovering IL-2 which involves an RP-HPLC step performed under similar conditions.

E. Pharmacokinetics of PEGylated IL-2 compared to unmodified IL-2 in mice.

1. Intravenous administration

Pharmacokinetic data of unmodified IL-2 and two preparations of PEGylated IL-2 were obtained after intravenous administration of 12.5 μg of protein in D5W (5% dextrose in water) in each mouse in a total of 36 mice. Samples used for injections (100 μl bolus) are identified below and had the following activities.

| Sample | IL-2 Activity (BRMP Standards Units/mg IL-2) |
|---|---|
| A. Unmodified IL-2 (lot LP-263) | $5.98 \pm 0.46 \times 10^6$ |
| B. PEGylated IL-2 (from 10 moles PEG*/mole IL-2 reaction) | $12.19 \pm 4.14 \times 10^6$ |
| C. PEGylated IL-2 (from 50 moles PEG*/mole IL-2 reaction) | $4.37 \pm 0.23 \times 10^6$ |

Sample A was rendered free from aggregated material by injection in D5W containing 0.1% SDS final concentration. The PEGylated IL-2 samples (B and C) contained no SDS because these are completely soluble without aggregation under normal aqueous conditions.

Figure 3:
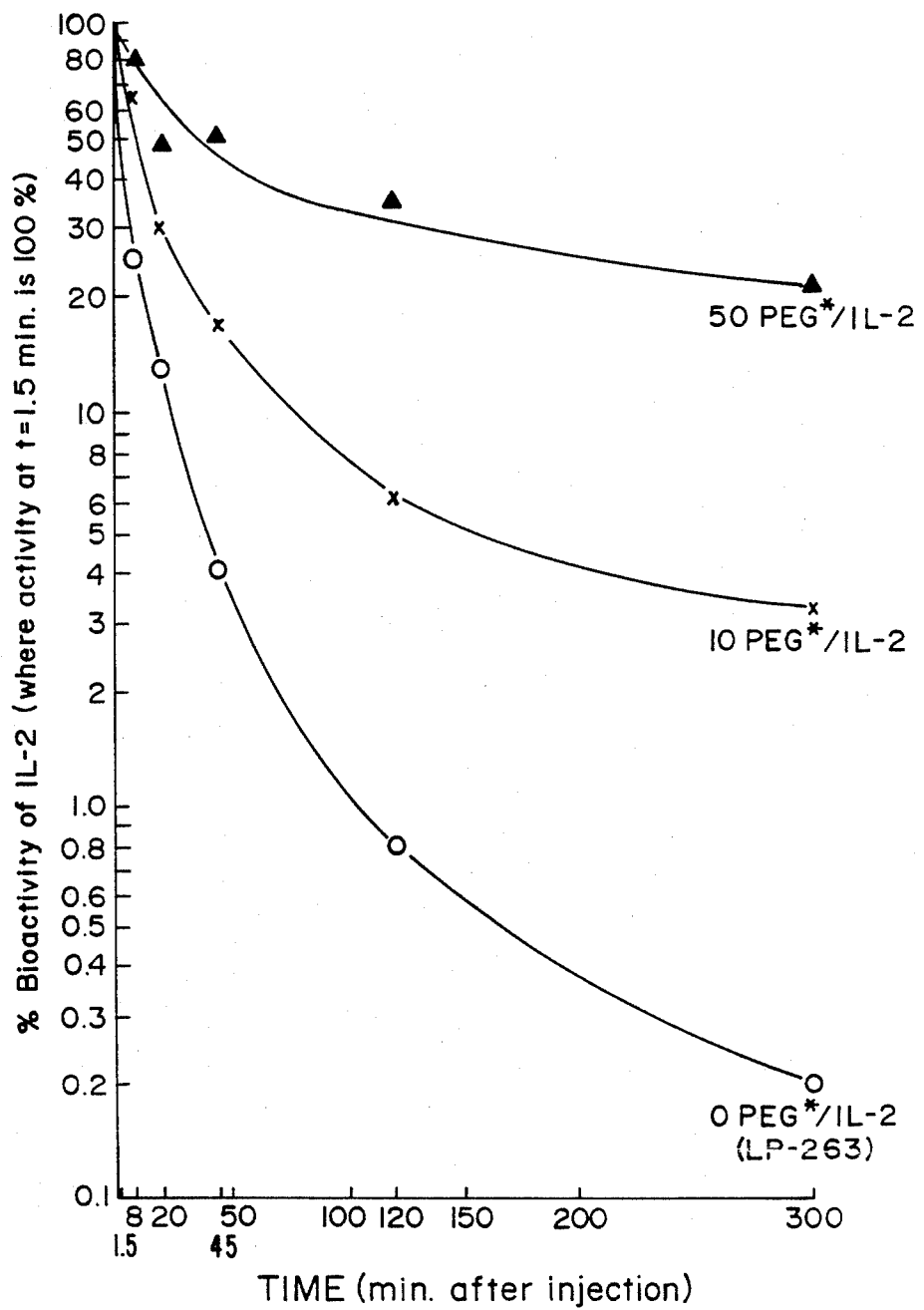
FIG. 3 depicts the pharmacokinetics of PEGylated and unmodified IL-2 after intravenous injection into mice.

Each mouse from three groups of twelve female Balb/C mice was injected with one of the three samples into the tail vein and all were bled retro-orbitally at 1.5 min. At various later times after injection 100 μl blood samples were removed retro-orbitally into heparinized capillary tubes. Plasma was prepared immediately by centrifugation (1 min.) and an aliquot was diluted into assay medium for bioassay as described in Example I.C. FIG. 3 shows the pharmacokinetics of unmodified IL-2 and two preparations of PEGylated IL-2 samples. The half-lives of the initial distribution of IL-2 from FIG. 3 (at 50% bioactivity) are the following:

| Sample | t ½ |
|---|---|
| A. Unmodified IL-2 | 2 min. |
| B. PEGylated IL-2 (10 PEG*/IL-2) | 10 min. |
| C. PEGylated IL-2 (50 PEG*/IL-2) | 35 min. |

Thus, PEGylation of IL-2 results in a five-fold increase in circulating half-life in mice using 10 PEG*/IL-2, as measured by cell proliferation assays, and a more dramatic 17-fold increase in circulating half-life using 50 PEG*/IL-2.

When unmodified IL-2, PEGylated IL-2 (from 10 moles PEG*/mole IL-2 reaction) and PEGylated IL-2 (from 50 moles PEG*/mole IL-2 reaction) were injected intravenously into twelve mice per each type of IL-2, the percent recovery of bioactivity of total injected units of IL-2 at 1.5 minutes after injection is indicated below:

| Sample | % Recovery of IL-2 Bioactivity |
| --- | --- |
| A. Unmodified IL-2 | 57 |
| B. PEGylated IL-2 (10 PEG*/IL-2) | 72 |
| C. PEGylated IL-2 (50 PEG*/IL-2) | 100 |

These results show a dramatic increase in percent recovery of IL-2 bioactivity with the degree of modification by PEG*, with 100% recovery occurring at the modification level of 50 moles PEG* per mole IL-2.

2. Subcutaneous administration.

Pharmacokinetic data of unmodified and PEGylated IL-2 were obtained after subcutaneous administration in 48 mice of 12.5 μg protein in sterile water. Samples used for scapular subcutaneous injection (single 100 μl bolus) in mice included unmodified IL-2, PEGylated IL-2 (from 20 moles PEG*/mole IL-2 reaction), and PEGylated IL-2 (from 50 moles PEG*/mole IL-2 reaction). All three samples were at 0.125 mg/ml. The unmodified IL-2 sample contained 0.1% SDS due to its insolubility in aqueous solution at neutral pH.

Figure 4:
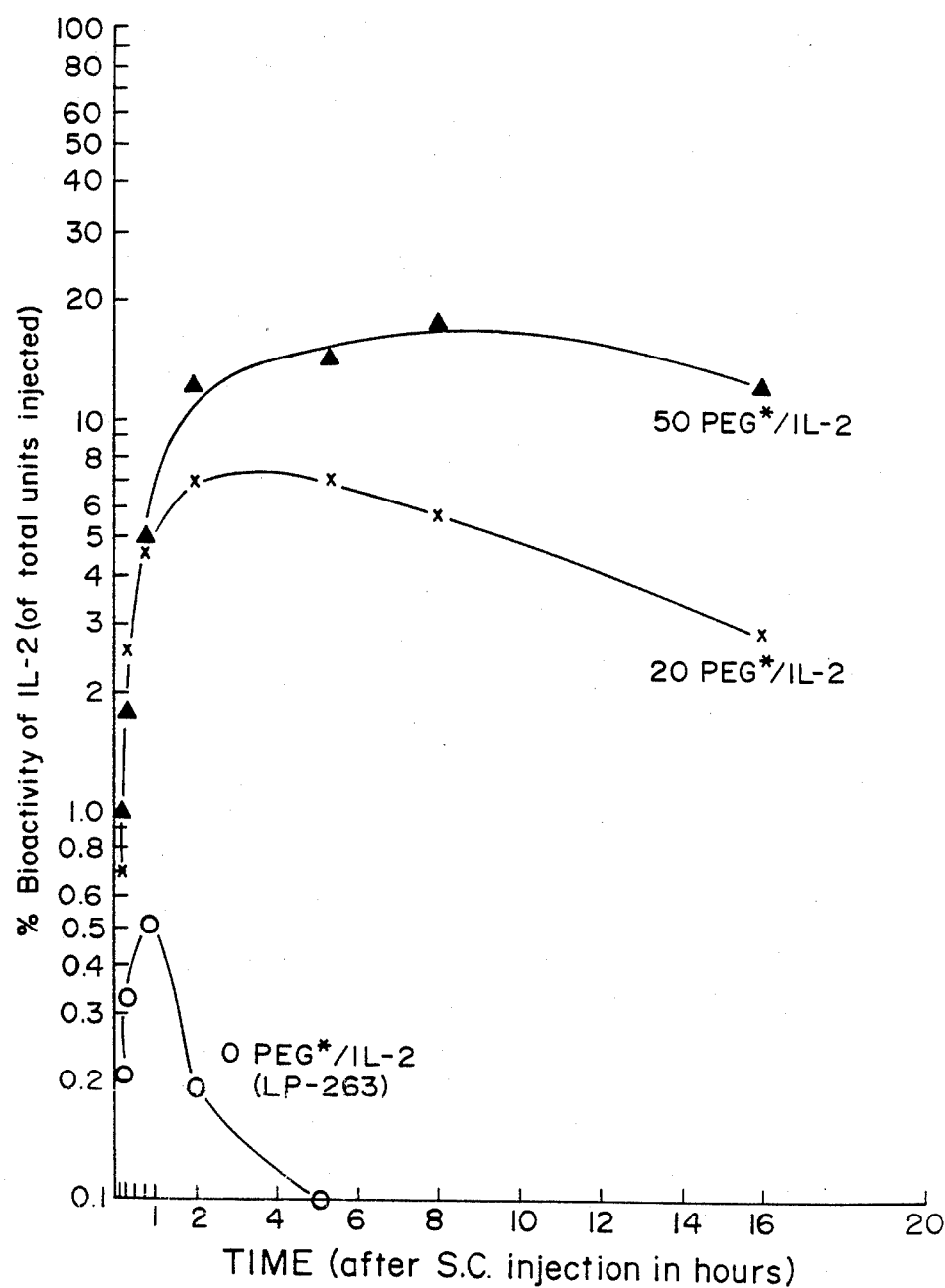
FIG. 4 shows the pharmacokinetics of PEGylated and unmodified IL-2 after subcutaneous injection into mice.

At various time points 100 μl samples were removed retroorbitally into heparinized tubes as previously described. Plasma was prepared and aliquoted for bioassay. The 45 min. time point had 16 mice for each of the three samples. All other time points had 2-5 mice per sample. FIG. 4 shows the pharmacokinetics of unmodified and PEGylated IL-2's after subcutaneous injection into mice. Not only was the maximum percentage of the total IL-2 bioactivity injected found in the plasma much higher for the PEGylated molecules as indicated below, but the clearance rate of PEGylated IL-2 was significantly lowered (see FIG. 4).

| Sample | Maximum % IL-2 Bioactivity Found in the Plasma |
| --- | --- |
| A. Unmodified | 0.5 |
| B. PEGylated IL-2 (20 PEG*/IL-2) | 7.0 |
| C. PEGylated IL-2 (50 PEG*/IL-2) | 17.5 |

F. Immune response in rabbits after injections of PEGylated IL-2 and unmodified IL-2.

The study had three groups, with four rabbits in each group.

Group A were rabbits injected with unmodified post-diafiltered des-alanyl, ser$_{125}$ IL-2 from the production process described hereinabove (lot LP 304). Group B were rabbits injected with PEG/IL-2 prepared from lot LP 304 using 20-fold excess PEG* as described above. Group C were rabbits injected with PEG/IL-2 also prepared from LP 304 using 50-fold excess PEG*. Each IL-2 preparation was diluted in sterile water prior to injection.

Female New Zealand White rabbits (weighing ~2.2 kg) were each injected intramuscularly at two sites, 0.5 ml (1-2 × 10$^5$ units) per site of the appropriate IL-2 or PEGylated IL-2.

At various time intervals, all of the rabbits were bled from the marginal ear vein or middle ear artery. The blood was allowed to clot and centrifuged to obtain serum. Aliquots of the sera were diluted 5-fold into IL-2 assay medium and bioassayed by the cell proliferation assay of Example I.C. The pharmacokinetic profiles of IL-2 and PEGlyated IL-2 in the circulating blood after intramuscular injection were similar to those obtained with mice.

One week after the above injections, all rabbits were given a second series of injections, intramuscularly, with the appropriate IL-2 or PEGylated IL-2. The units injected were the same as above.

Three weeks after the first injections, all rabbits were boosted with the appropriate unmodified IL-2 or PEGylated IL-2 at 1-2 × 10$^4$ units/kg. Antigen-specific antibody response was measured in the sera (obtained as described above) at regular intervals by ELISA assays, using horseradish peroxidase linked goat antirabbit IgG as the labeled reagent and orthophenylenediamine as the substrate. Absorbance was measured at 492 nm. The antigens were coated on two types of ELISA plates, polystyrene and polyvinyl, obtained from Dynatech Laboratories, Inc. The antigens tested against the sera were unmodified IL-2 (LP 304), PEG/IL-2 (20-fold excess PEG*) and PEG/IL-2 (50-fold excess PEG*). The results at five weeks after the first injections were as follows:

Group A These rabbits had all developed IL-2-specific IgMs, seen in dilutions to 10$^4$-10$^5$ in ELISAs. Two (A3 and A4) of the four rabbits also had high IL-2-specific IgGs up to 10$^4$ dilutions. Rabbit A2 had slightly lower levels of IgG. Rabbit A1 had the least IL-2-specific IgGs.

Group B These rabbits developed no detectable IL-2-specific IgGs. All had IL-2-specific IgMs detected to 10$^2$ dilutions in ELISA assays. These assays were repeated using PEG/IL-2 as the antigen on the ELISA plates, with the same result.

Group C These rabbits had no detectable IL-2-specific IgGs. All had IL-2-specific IgMs detected up to 10$^2$ dilutions in ELISA assays done with PEG/IL-2 as the antigen.

These studies indicate that the antigen-specific IgG response is reduced in the cases where PEG/IL-2 is the antigen, whereas with unmodified IL-2, antigen-specific IgGs are developed with time.

G. Efficacy studies of PEGylated IL-2 in Balb/c mice using a Meth A model

In this experiment where mice were dosed daily, PEG/IL-2 was strongly effective against Meth A sarcoma at doses where unmodified IL-2 had only a slight effect.

66 Balb/c mice were each injected subcutaneously at the back of the neck with 6 × 10$^5$ Methacholanthene-A (Meth A) mouse fibrosarcoma tumor cell line, obtained from Sloan-Kettering as a cell suspension from ascites fluid in Balb/c mice. The mice were segregated into three groups with similar numbers of large, medium, and small tumors (5-100 mm). The three groups were then injected intraperitoneally with test material. Group A received 0.5 ml of PBS containing 0.01 mg/ml PEG (monomethyl 5000). Group B received 0.5 ml of tissue culture medium containing 10% calf serum + 3 μg of the PEG*/IL-2 obtained using 20-fold excess of PEG* over IL-2. Group C received tissue culture medium containing 10% calf serum + 3 μg of the unmodified postdiafiltered des-ala$_1$, ser$_{125}$ IL-2 as described above.

The three groups were injected daily for 7 days. The mice were weighed and their tumor volumes measured on four days.

On day 8, the three groups differed in body weight.

| | | |
|---|---|---|
| PEG control | 26.0 g | |
| PEG*/IL-2 | 21.1 g | |
| IL-2 | 23.6 g | |

| | Day 0 Tumor Volume ($mm^3$) | Day 6 Tumor Volume ($mm^3$) | Day 8 Tumor Volume ($mm^3$) | Day 9 Tumor Volume ($mm^3$) |
|---|---|---|---|---|
| Group A (PEG control excipient) | 138 + −48 | 3259 + −919 | 5597 + −1877 | 7333 + −1403 |
| Group B (PEG/IL-2) | 129 + −42 | 424 + −129 | 341 + −218 | 353 + −148 |
| Group C (IL-2) | 130 + −63 | 2523 + −808 | 2034 + −997 | 4405 + −1471 |

On day 8, the mice treated with formulated IL-2 showed 64% tumor growth inhibition. However, by day 9 the inhibition was only 40% and the tumors were growing rapidly. The group was sacrificed to restrict suffering. The mice treated with PEG*/IL-2 showed 94% tumor growth inhibition both on day 8 and day 9. These mice also were sacrificed to restrict suffering.

EXAMPLE III

Preparation of PEGylated IL-2 With 350 Molecular Weight PEG

A. Preparation of PEG-Ester.

A linear, monomethyl-substituted ester of PEG of molecular weight 350 was obtained by the following method.

A total of 10 g monomethyl PEG-350 from Aldrich Chemical Co. was heated to 110° C. To this was added 14.3 g succinic anhydride (Aldrich). The mixture was stirred overnight at 110° C. and then cooled. Benzene was added and the benzene solution filtered. The reagent was isolated from the filtrate.

Two grams of the resulting PEG-350-succinate was mixed with 25 ml dimethyl formamide, 3.531 g dicyclohexylcarbodiimide and 6.914 g HNSA prepared as described in Example I. The mixture was stirred at room temperature for 48 hours in the dark and filtered. To the filtrate was added slowly one liter of ether to precipitate the reagent. A total of 150 mg of the crude mix was added to 1 ml $H_2O$, centrifuged and decanted. The supernatant was applied to a Sephadex G-25 column in water and the appropriate fractions were pooled and lyophilized. The resulting purified product is designated hereinafter as PEG*.

B. Conjugating of PEG* to IL-2.

The des-ala$_1$ser$_{125}$IL-2 prepared as described in U.S. Pat. Nos. 4,518,584 and 4,572,798, supra, was employed for this example. To 0.4 mg of this purified IL-2 in 1.0 ml buffer (0.1M sodium borate, pH 9, 0.1% SDS) was added freshly prepared aqueous PEG* in a molar ratio of 10 moles PEG* per mole of IL-2. After thorough mixing the solutions were stirred at 32° C. for 15 minutes, 1 hour, 5 hours, and 20 hours. At each time point, 125 µl of the solution was removed and added to 40 µl of 1 mg/ml epsilon-$NH_2$-caproic acid and stored at 4° C.

C. Characterization of PEGylated IL-2.

SDS-PAGE (14%, reducing) analysis of the products from reaction B revealed that there was a substantial amount of modification which occurred by 15 minutes.

The PEG-350 IL-2 was active as tested by the IL-2 cell proliferation bioassay in vitro mentioned above in Example I.C.

D. Pharmacokinetics of PEGylated IL-2 Compared to Unmodified IL-2 in Mice.

PEG-350 IL-2 and unmodified IL-2 were injected intravenously into mice for pharmacokinetic analysis in a similar manner as described above in Example II.E. The results are shown in Table II.

TABLE II

Pharmacokinetics of PEGylated IL-2 (PEG-350 IL-2)

| | BRMP Standards Units*/% Recovered | |
|---|---|---|
| Time | Unmodified IL-2 | IL-2 PEG* |
| 0 min. (total units injected) | 176,913 | 80,046 |
| 1.5 min. | 81,880/ 46.3 | 25,035/ 31.3 |
| 8 min. | 9602/ 5.43 | 3158/ 3.94 |
| 20 min. | 4950/ 2.80 | 2772/ 3.46 |
| 45 min. | 1178/ 0.67 | 564/ 0.70 |
| 1 hour | 212(2)**/ 0.12 | 129/ 0.16 |
| 2 hour | 46(2)**/ 0.03 | 0 |
| 3 hour | 0 | 0 |

*These units are units in mouse (BRMP units × 20-fold dilution).
**Parentheses indicate if there were fewer than 4 mice in the group.

EXAMPLE IV

Preparation of PEGylated IL-2 with 400 and 1000 Molecular Weight PEG

IL-2 derivatives of linear dihydroxy (unsubstituted) PEG of molecular weight 400 and 1000 were prepared generally by the method described in Example III using unsubstituted PEG-400 and PEG-1000, respectively.

EXAMPLE V

Preparation of PEGylated IL-2 with 10,000, 20,000 and 35,000 Molecular Weight PEG An IL-2 derivative of linear, monomethyl-substituted PEG of molecular weight 10,000 was obtained generally following the method described in Example I.A. using PEG 10,000 from Union Carbide. IL-2 derivatives of dihydroxy PEG of molecular weights 20,000 and 35,000 were obtained following a method similar to Abuchowski et al., supra, referred to in Example I.A. (using base in a solvent at room temperature rather than an elevated temperature) using PEG-20,000 and PEG-35,000 from Fluka. The resulting modified IL-2 proteins were bioactive as assayed by the cell proliferation assay described above.

EXAMPLE VI

Preparation of PEGylated Interferon-β (IFN-β) Using PEG-5000

Preparation of activated PEG-ester and conjugation of the activated PEG-ester to RP-HPLC purified recombinant IFN-β where the cysteine residue at position 17 is replaced by a serine residue (ser$_{17}$ IFN-β), as described in U.S. Pat. No. 4,518,584, were carried out essentially as described for IL-2 in Example I.A. and I.B., in reactions containing 0, 10, 20 or 50 moles PEG* per mole of IFN-β. Separation of PEGylated IFN-β from unmodified IFN-β can be accomplished using molecular exclusion chromatography using a Sephacryl S-200 column in 50 mM sodium acetate pH 5 with 0.1% SDS. Aliquots from the S-200 fractionation were assayed for IFN-β antiviral activity using the cytopathic effect (CPE) assay method described generally by W. E. Stewart, "The Interferon System," Springer-Verlag, p. 17–18 (1979) and found to be active as described in Example VII. The CPE assay functions on the principle that interferon protects cells treated therewith from the effects of virus. Cells more resistant to the virus will survive, whereas those which are sensitive to the virus will experience the cytopathic effect and die.

EXAMPLE VII

Characterization of PEGylated IFN-β Modified With PEG-5000

A. Size characterization of modified IFN-β products from reactions with varying PEG* to IFN-β molar ratios.

Figure 5:
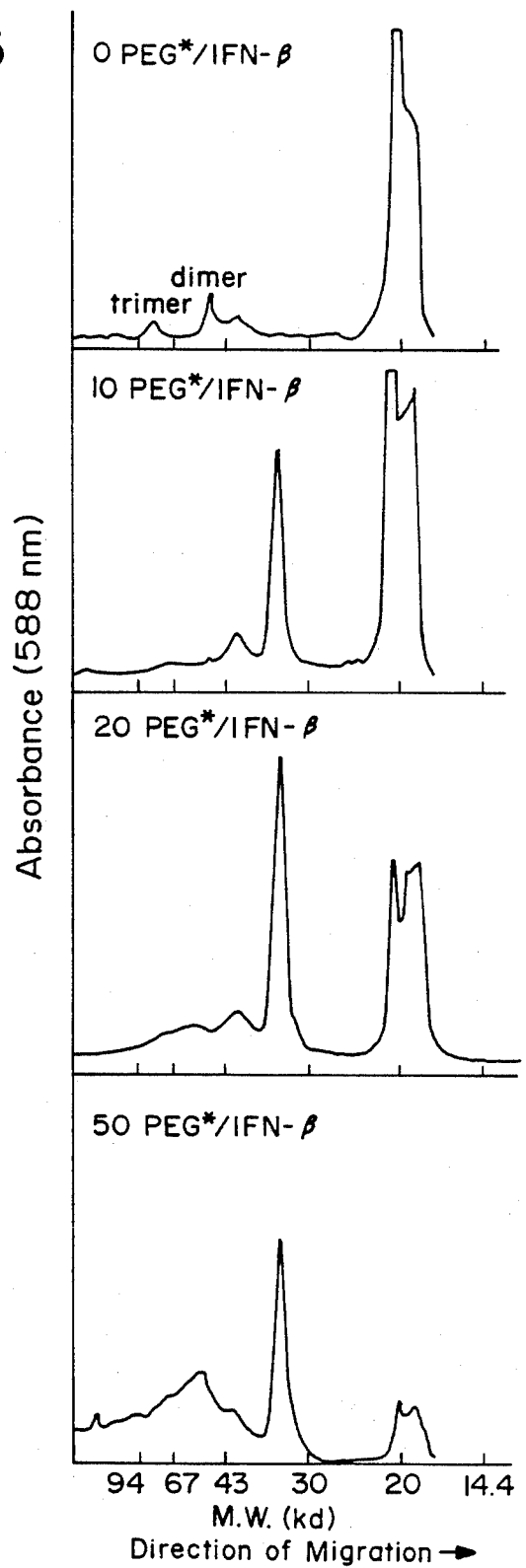
FIG. 5 shows densitometry scans of 41% nonreducing SDS-polyacrylamide gels for molecular weight analysis of PEGylated IFN-$\beta$ obtained from reactions at 0, 10, 20 and 50 moles PEG* per mole of IFN-$\beta$.

SDS-PAGE (14%, nonreducing) of the products from reactions described in Example VI containing 0, 10, 20 or 50 moles PEG* per mole of IFN-β shows, as in the case of IL-2, an increasing degree of modification with increasing PEG* to IFN-β molar ratios. Densitometry scans (FIG. 5) illustrate a decrease in the amount of unmodified IFN-β running at a molecular weight of 20,000 with increasing PEG* to IFN-β molar ratios. A discrete species with an apparent molecular weight of 30–35,000 was present after PEG-modification of IFN-β at all three molar ratios tested (10 PEG*/IFN-β, 20 PEG*/IFN-β and 50 PEG*/IFN-β). An increase in higher molecular mass species, probably representing more highly modified IFN-β molecules, was evident in the reaction carried out at 50 moles PEG* per mole of IFN-β.

B. Bioactivity of PEGylated IFN-β compared to unmodified IFN-β.

Fractions of the S-200 separation of the PEGylated reactions containing 0, 10, 20 or 50 moles PEG* per mole of IFN-β were assayed for antiviral activity as described in Example III. The bioactivities of PEGylated IFN-β obtained from all three modification reactions were comparable to unmodified IFN-β, as shown in Table III.

TABLE III

| Bioactivities of Unmodified IFN-β and PEGylated IFN-β As Measured by CPE Assay | |
| --- | --- |
| Mole of PEG* Initially Added Per Mole IFN-β | Bioactivity (Units/mg) |
| 0 | $2.2 \pm 0.6 \times 10^7$ |
| 10 | $2.2 \pm 1.6 \times 10^7$ |
| 20 | $2.0 \pm 0.1 \times 10^7$ |
| 50 | $4.1 \pm 0.8 \times 10^7$ |

C. Solubility of PEGylated IFN-β Compared to Unmodified IFN-β.

Figure 6:
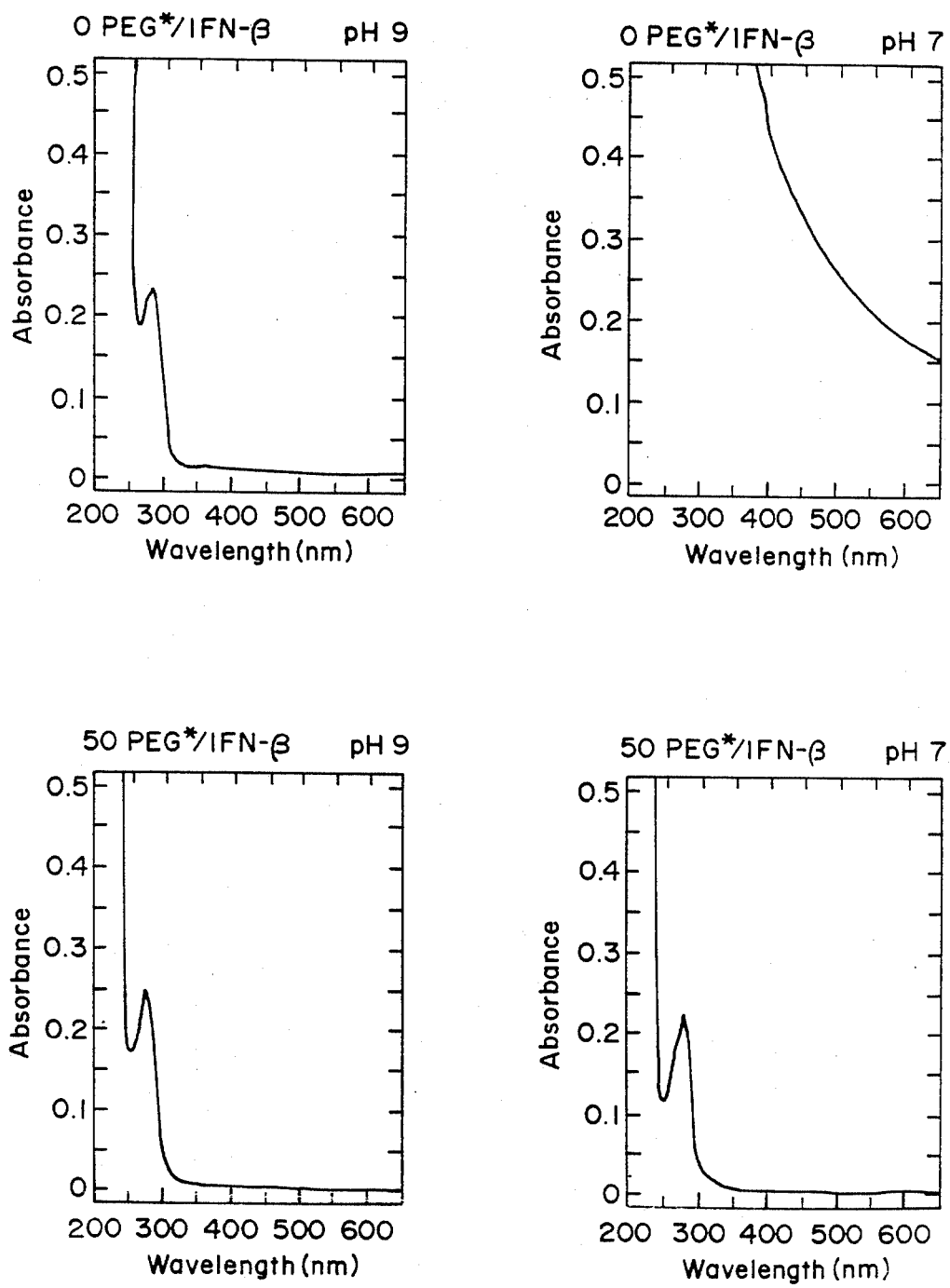
FIG. 6 illustrates the solubility of PEGylated IFN-$\beta$ compared to unmodified IFN-$\beta$ at two different pHs by absorbance scan from 200 to 650 nm.

After the modification reaction and the S-200 fractionation, SDS was removed using Sephadex G-25 chromatography similar to that described in Example I, all of the PEGylated IFN-β and the unmodified IFN-β were each adjusted to pH 7. Whereas the PEGylated IFN-β remained in solution as indicated by absorbance scan from 200 to 650 nm, the unmodified IFN-β precipitated out of solution at pH 7 (FIG. 6). Both modified and unmodified IFN-β were soluble at pH 9. Similar results were obtained for all PEGylated IFN-β samples tested.

D. Pharmacokinetics of PEGylated IFN-β Compared to Unmodified IFN-β.

In vivo half-life was improved similarly to that of IL-2 in rats and mice using PEGylated IFN-β versus unmodified IFN-β.

EXAMPLE VIII

Preparation and Characterization of PEGylated Ricin A

A. Preparation of PEGylated Ricin A Chain.

A soluble recombinant ricin A which requires no solubilization to be subjected to purification and to display cytotoxicity was prepared in accordance with the procedure described in copening U.S. application Ser. No. 837,583 filed Mar. 7, 1986, the disclosure of which is incorporated herein by reference. Briefly, when the coding sequence for ricin A was placed into direct reading frame with the DNA encoding leader sequence of phoA to form a putative fusion peptide, so that the leader sequence is the N-terminal portion of a leader/ricin A chimera, the ricin A sequences so disposed result in the soluble cytotoxic material.

Expression vectors containing the genes for the precursor proteins contained in pRT3 (ATCC Deposit No. 67,207 deposited Mar. 7, 1986), pRT17 (ATCC Deposit No. 67,026 deposited Mar. 7, 1986), and pRT38 (ATCC Deposit No. 67,025 deposited Mar. 7, 1986) or their mutagenized forms were constructed. Transforming host cells with these expression vectors resulted in solubilization of the precursor protein encoded. The arg-arg modified precursor was cleaved with trypsin; the A and B portions of the precursors were produced as separate proteins, as herein described.

In the phoA expression system, the essential component is the terminated phoA leader sequence upstream of, proximal to, and out of frame with the ricin A encoding sequence, wherein the ricin A encoding sequence is initiated by an ATG codon. The two coding sequences must be, of course, provided with a compatible bacterial promoter, which was the phoA promoter already associated with the leader. Additionally, production was improved in the presence of a positive retroregulator sequence which was the positive retroregulator sequences associated with the crystal protein of *B. thuringiensis*, which are described extensively in copending U.S. Ser. No. 646,584, filed Aug. 31, 1984 and incorporated herein by reference. This was provided on bacterial transport vectors which included replicons and selectable markers.

The vectors were then used to transform a suitable procaryotic host, which was grown under conditions suitable for the particular host chosen, most frequently under conditions whereby the promoter placed in control of the expression system was suppressed. The production of the ricin A was then induced by providing conditions which effect expression under control of the chosen promoter and the production permitted to proceed for sufficient time to effect a desired accumulation of product. The protein product was then isolated by disrupting the cells and the cellular debris was removed. The ricin A produced was then further purified using standard techniques known in the art as applied to freely soluble proteins. However, the efficiency of the extraction and purification was enhanced by treating partially clarified extract with phenyl sepharose. The solubility of the ricin A in the sonicate (once separated from the membrane or other associated materials) was shown by its ability to remain in the supernatant when the sonicate was subjected to centrifugation at high speed, 100,000×g for 30 minutes, to spin down insoluble proteins.

A total of 2 ml of this soluble ricin A (at 9.0 mg/ml) was rereduced by adding 2 μl of fresh β-mercaptoethanol (to 0.1%) and incubating at room temperature overnight. The 2 ml of reduced ricin A was applied to a G-25 column (Pharmacia) equilibrated with 0.10M NAPO₄ pH 8.0, followed by 0.5 ml of buffer to make 2.5 ml sample application volume. The next 3.0 ml of eluate (buffer was applied) was collected as desalted ricin A.

1.0 ml of desalted ricin A (about 6 mg) was transferred to a 1.5 ml microfuge tube. To the ricin A was added 4.5 mg of N-hydroxysuccinimide ester of polyethylene glycol 2000 (activated PEG) obtained as described in Example I.A. The 4.5 mg of activated PEG represented an 11-fold excess of the activated PEG over the ricin A.

The activated PEG was dissolved in the ricin A solution by gentle mixing. At various time points 100 μl aliquots of the reaction mixture were desalted by the following procedure on G-25 columns to remove unreacted activated PEG and stop the PEGylation reaction:
100 μl PEG/ricin A applied
2.4 ml 0.10M NaPO₄ pH 8.0 applied
1.1 ml 0.10M NaPO₄ pH 8.0 applied
and eluate collected as desalted ricin A Time points taken were: 10', 20', 30', 45', 1 hour, 2 hours, 3 hours, 4 hours and 5 hours.

The reaction mixture was maintained on ice from time 0.

A 15% mini-gel was run to determine the degree of PEGylation. The results indicated that the PEGylation appeared to have worked well and the reaction occurred quickly.

A new sample of PEGylated ricin A was prepared for conjugation to an antibody. About 40 mg of the ricin A described above was mixed with about 10 ml of Tris buffer, pH 8.5 with 1% β-mercaptoethanol. This was concentrated to about 5 ml and desalted in an EDTA buffer on two G-25 columns to yield 6.37 ml total eluate. A total of 24.6 mg of N-hydroxysuccinimide ester of PEG (about 2000) was added to the ricin A and the mixture was allowed to react for 15 minutes on ice. (This amounts to a 10-fold excess of the activated PEG.)

The PEGylated ricin A was desalted over three G-25 columns, to yield a final eluate volume of 9.70 ml. β-Mercaptoethanol was added to 5 mM (about 0.05%). The PEGylated ricin A mixture was stored at 4° C.

A total of 50 μg of PEGylated ricin A mixture was injected into a preparative Zorbax GF-250 sizing column (DuPont) at a flow rate of 1 ml/min. using a buffer of 50 mM (NH₄)₂SO₄, 40 mM NaPO₄, pH 6.5.

The first peak was PEGylated ricin A, as determined by a 13.5% Minigel run of 5 ml fractions from a preparative fractionation.

The pool obtained in the first run was concentrated to about 2 ml and then purified by HPLC on a Zorbax GF-250 column by monitoring the absorbance at 280 nm. Fractions 15-23 of each run were pooled as PEGylated ricin A.

The molecular weight of the PEGylated ricin A was then determined by running a molecular weight standard (BioRad) on HPLC, under conditions similar to the purification method described above. A linear regression was performed, indicating that the PEGylated ricin A had apparent molecular weights of about 22K (1-mer), 44K (2-mer), and 59K (higher mers).

B. Characterization of PEGylated Ricin A.

Aliquots from the 2 mg PEGylated ricin A Zorbax GF-250 run were tested for bioactivity in a reticulocyte assay (translation) using a kit manufactured by Promega Biotec. The samples given were fraction 28 (high molecular weight), 34 (2-mer), 40 (1-mer), and some unpurified PEGylated ricin A/unmodified ricin A mix. The rabbit reticulocyte cell-free translation system assay measures protein synthesis by incorporation of radioactive methionine.

The results, shown in Table IV, indicated that only the purified 1-mer shows inhibition approaching that of free ricin A. The 2-mer and higher mer fractions showed greatly reduced inhibition as measured by elevated Inhibitory Doses at 50% (ID50).

TABLE IV

| Material | ID50 (ng/ml) | ID50 (M) |
| --- | --- | --- |
| Ricin A | 0.16 | $5.2 \times 10^{-12}$ |
| Higher molecular weight | 158.5 | $5.2 \times 10^{-9}$ |
| 2-mer | 5011.9 | — |
| 1-mer | 3.16 | $103.6 \times 10^{-12}$ |

Thus, it appears that it may be necessary to PEGylate ricin only to produce 1-mers and to remove higher mers from the mixture.

The solubility benefit of the PEGylation was observed—the concentration of the PEGylated ricin A to 20 mg/ml which was achieved was not possible using un-PEGylated ricin A.

C. Conjugation of PEGylated Ricin A to Antibody.

A breast monoclonal antibody designated 520C9 described more fully in copending U.S. application Ser. No. 842,476 filed Mar. 21, 1986 was deposited as Accession No. HB8696 on Jan. 8, 1985 in the American Type Culture Collection, Rockville, MD. This antibody was reacted with 5,5'-dithiobis-(2-nitrobenzoic acid) at room temperature and then chilled, and then sufficient 2-iminothiolane (IT) was added to give 2.5 IT molecules per antibody molecule, as described in Ser. No. 842,476, supra.

A total of 166 μl of propylene glycol was added to 0.84 ml of the IT-derivatized antibody. The 2.32 ml of PEGylated ricin A chain described above was added to initiate the conjugation reaction. The mixture was incubated at room temperature for two hours.

The conjugation reaction mixture was applied to a Zorbax-GF-250 sizing (gel filtration) HPLC column using an eluting buffer of 0.15M NaPO₄, pH 8.0. A total of 78% recovery of the purified immunoconjugate was obtained from the column.

D. Characterization of Conjugate.

1. Ribosomal Translation Assay.

The conjugate pool was filter-sterilized under a sterile hood into a sterile tube from which aliquots were sterilely pipetted into various sterile microfuge tubes. A 100 μl aliquot of final sterifiltered immunotoxin was incubated with purified extracts from rabbit reticulocytes. ³⁵S methionine, mRNA and other factors for mRNA synthesis. The assay was measured without and with an inhibitor of ribosomal translation. The dose response curve measures protein synthesis. Control samples included a conjugate of non-PEGylated immunotoxin, ricin A chain, and PEGylated ricin A chain. The results were as follows:

| Test Material | ID50 (M based on Ricin A Chain) |
|---|---|
| Ricin A chain | $5.9 \times 10^{-12}$ |
| PEGylated ricin A chain | $52.0 \times 10^{-12}$ |
| Conjugate of ricin A chain and 520C9 | $60.8 \times 10^{-12}$ |
| Conjugate of PEGylated ricin A chain and 520C9 | $141.0 \times 10^{-12}$ |

This assay indicated that the ID50 for PEGylated conjugate and non-PEGylated conjugate was 15.85 and 7.94 ng/ml, respectively. Because the accuracy of this assay is no better than about +/−100%, the inhibition for both is identical. It is apparent that addition of antibody alone to ricin A chain reduces the ID50 compared to non-conjugated ricin A. Thus, PEGylation does not impair ricin A activity more than addition of antibody. PEGylation of the immunotoxin rather than just the toxin is expected to improve the results.

2. In Vitro Cytotoxicity Assay.

Forty thousand test breast cancer cells (from cell line SKBR3-publicly available) in 1 ml medium were added to a set of 8 ml glass vials, followed by the addition of PEGylated and non-PEGylated conjugate dilutions (in phosphate buffered saline (PBS) containing 100 μg/ml bovine serum albumin (BSA)). After incubation at 37° C. for 22 hours, the medium was aspirated, the monolayers were washed with PBS, and methionine-free medium supplemented with $^{35}$S methionine was added. The vials were further incubated for two hours at 37° C., the medium was removed, and the cells were washed twice with 2 ml of 10% trichloroacetic acid containing 1 mg/ml methionine. The cells were dried, scintillation fluid was added, and the radioactivity was counted in a scintillation counter. Cytotoxicity was expressed as the tissue culture inhibitory dose of conjugate that resulted in 50% of control (untreated) protein synthesis (TCID 50%).

The results of the assay were the following:

| Conjugate | TCID 50% (nM) |
|---|---|
| Non-PEGylated | 0.216 |
| PEGylated | <0.422 |

The accuracy of this assay is also no better than about +/−100%, and thus the TCID values of both are identical. With respect to cellular intoxication, the rate-limiting step does not appear to involve ricin A chain activity, but rather some other event, quite possibly conjugate binding, translocation, and/or intra-cellular routing.

EXAMPLE IX

Preparation and Characterization of IL-2 Modified With Polyoxyethylated Glycerol (POG)

A. Preparation of Active POG-IL-2.

Polyoxyethylated glycerol (POG) of molecular weight 5000 was custom synthesized by Polysciences. To 10 g of POG was added 2.28 g glutaric anhydride (a ten-fold excess over POG). The mixture was stirred for two hours at 110° C. and cooled. This was dissolved in 20 ml $CHCl_3$ and poured slowly into 500 ml ether with vigorous stirring. The product was collected and rinsed with ether to yield about 90% POG-glutarate product. This product was reacted with N-hydroxysuccinimide as described in Example I.A. to yield the active ester POG-glutaryl N-hydroxysuccinimide (POG*). Then 20 ml of 0.25 mg/ml IL-2 in 0.1M sodium borate, pH 9, 0.1% SDS as described in Example I.B. was reacted with 5 mg of the POG* at room temperature for 30 minutes.

Ten ml of the reaction mixture was concentrated to 2 ml and applied to a Sephadex G-25 column in 10 mM sodium borate, pH 9. This was adjusted to pH 7 (soluble) and concentrated. To 2 ml of the concentrate was added a solvent consisting of 1.7M $(NH_4)_2SO_4$, 50 mM sodium phosphate, pH 7. This was then applied to a phenyl-TSK column at 0° C. The SDS-PAGE (14%, reducing) of the fraction indicated good separation.

The other 10 ml of POG-IL-2 was concentrated to 3 ml after adjusting to pH 5. This was applied to a Sephacryl S-200 column. SDS-PAGE (14%, reducing) of the fractions revealed a homogeneous POG-IL-2 product.

B. Characterization of POG-IL-2.

The fractions from the S-200 separation of the reaction mixture were assayed for bioactivity as described in Example I.C. The results are indicated in Table V.

TABLE V

| Sample | Bioactivity (BRMP Standards Units/mg IL-2) |
|---|---|
| Unmodified IL-2 (average) | $12 \times 10^6$ |
| Two pooled fractions with largest amount of POG-IL-2 (average) | $15 \times 10^6$ |

Deposits

The plasmids with sequences used to prepare ricin A chain and the hybridoma which produces antibody 520C9 were deposited in the American Type Culture Collection (ATCC), 12301 Parklawn Drive, Rockville, Md. 20852-1776, USA. The ATCC accession numbers and deposit dates for the deposited samples are:

| Vector/Hybridoma Designation | Deposit Date | Accession No. |
|---|---|---|
| 520C9 | 1/8/85 | HB 8696 |
| pRT3 | 3/7/86 | 67,027 |
| pRT17 | 3/7/86 | 67,026 |
| pRT38 | 3/7/86 | 67,025 |

The deposits above were made pursuant to a contract between the ATCC and the assignee of this patent application, Cetus Corporation. The contract with ATCC provides for permanent availability of the progeny of these plasmids and the cell line to the public on the issuance of the U.S. patent describing and identifying the deposit or the publications or upon the laying open to the public of any U.S. or foreign patent application, whichever coms first, and for availability of the progeny of these plasmids and the cell line to one determined by the U.S. Commissioner of Patents and Trademarks to be entitled thereto according to 35 USC §122 and the Commissioner's rules pursuant thereto (including 37 CFR §1.14 with particular reference to 886 OG 638). The assignee of the present application has agreed that if the plasmids and the cell line on deposit should die or be lost or destroyed when cultivated under suitable conditions, they will be promptly replaced on notification with a viable culture of the same plasmids and cell line.

In summary, the present invention is seen to provide a pharmaceutical composition wherein a biologically active specific protein selectively conjugated to a PEG homopolymer or a polyoxyethylated polyol and thereby made soluble or more soluble in an aqueous medium at physiological pH is dissolved in such medium. The conjugation serves not only to solubilize the normally hydrophobic water-insoluble protein in water at pH 6-8, but also increases its physiological half-life and may decrease its immunogenicity by decreasing or eliminating aggregation of the normally hydrophobic protein or by shielding its antigenic determinants. Without the conjugation, the protein must be solubilized by addition of solubilizing agents such as detergents or denaturants, by raising the pH in combination with addition of a stabilizer or by lowering the pH.

The foregoing written specification is considered to be sufficient to enable one skilled in the art to practice the invention. The present invention is not to be limited in scope by the plasmids and cell line deposited, since the deposited embodiments are intended as a single illustration of one aspect of the invention and any plasmids and cell lines which are functionally equivalent are within the scope of this invention. The deposit of materials herein does not constitute an admission that the written description herein contained is inadequate to enable the practice of any aspect of the invention, including the best mode thereof, nor are they to be construed as limiting the scope of the claims to the specific illustrations which they represent. Indeed, various modifications of the above-described modes for carrying out the invention which are obvious to those skilled in the field of pharmaceutical formulation or related fields are intended to be within the scope of the following claims.

What is claimed is:

1. A pharmaceutical preparation comprising a nontoxic, inert, pharmaceutically acceptable aqueous carrier medium in which is dissolved an immunotherapeutic effective amount of biologically active, selectively conjugated, recombinant interleukin-2 protein, wherein the protein is covalently conjugated via up to ten amino acid residues on the protein to a water-soluble polymer selected from the group consisting of polyethylene glycol homopolymers and polyoxyethylated polyols, wherein said homopolymer is unsubstituted or substituted at one end with an alkyl group and said polyol is unsubstituted and wherein said protein in its unconjugated form is normally hydrophobic.

2. The preparation of claim 1 wherein said polymer has a molecular weight of about 300 to 100,000.

3. The preparation of claim 1 wherein said polymer has a molecular weight of 350 to 40,000.

4. The preparation of claim 1 wherein said polymer is conjugated to the protein via the 4-hydroxy-3-nitrobenzene sulfonate ester or the N-hydroxysuccinimide ester of a carboxylic acid of said polymer.

5. The preparation of claim 4 wherein said polymer is an unsubstituted polyethylene glycol homopolymer, a monomethyl polyethylene glycol homopolymer or a polyoxyethylated glycerol.

6. The preparation of claim 1 wherein the medium is at a pH of about 5-8 and contains a buffer.

7. The preparation of claim 1 wherein the medium is at a pH of about 6.5-7.8 and contains a buffer.

8. The preparation of claim 1 wherein the protein is from a human source.

9. The preparation of claim 1 wherein said protein is selectively conjugated via one or two lysine residues on the protein.

10. The preparation of claim 1 wherein said protein is selectively conjugated via three to ten lysine residues on the protein.

11. The preparation of claim 8 wherein the protein is an interleukin-2 mutein.

12. The preparation of claim 11 wherein said mutein has the amino acid(s) which are at position(s) 104 and/or 125 in the native protein substituted with a neutral amino acid.

13. The preparation of claim 12 wherein said mutein is $ser_{125}$ IL-2, des-$ala_1$IL-2, des-$ala_1ser_{125}$ IL-2, des-$ala_1ala_{104}$IL-2, or des-$ala_1ala_{104}ser_{125}$ IL-2.

14. The preparation of claim 1 wherein said protein is selectively conjugated via up to ten lysine residues on the protein.

15. A composition comprising biologically active, normally hydrophobic recombinant interleukin-2 protein that is covalently conjugated via up to ten amino acid residues on the protein to a water-soluble polymer selected from the group consisting of polyethylene glycol homopolymers and polyoxyethylated polyols, wherein said homopolymer is unsubstituted or substituted at one end with an alkyl group and said polyol is unsubstituted.

* * * * *